(12) United States Patent
Clifford et al.

(10) Patent No.: US 7,248,172 B2
(45) Date of Patent: Jul. 24, 2007

(54) SYSTEM AND METHOD FOR HUMAN BODY FALL DETECTION

(75) Inventors: Michelle A. Clifford, Chandler, AZ (US); Rodrigo L. Borras, Marshalltown, IA (US); Leticia Gomez, San Diego, CA (US)

(73) Assignee: Freescale Semiconductor, Inc., Austin, TX (US)

( * ) Notice: Subject to any disclaimer, the term of this patent is extended or adjusted under 35 U.S.C. 154(b) by 210 days.

(21) Appl. No.: 11/087,339

(22) Filed: Mar. 22, 2005

(65) Prior Publication Data

US 2006/0214806 A1    Sep. 28, 2006

(51) Int. Cl.
*G08B 23/00* (2006.01)
(52) U.S. Cl. .................. 340/573.1; 340/573.7
(58) Field of Classification Search ............. 340/573.1, 340/573.7, 539.12, 539.11
See application file for complete search history.

(56) References Cited

U.S. PATENT DOCUMENTS 6,160,478 A * 12/2000 Jacobsen et al. ....... 340/539.12
6,433,690 B2 * 8/2002 Petelenz et al. ......... 340/573.1
7,095,331 B2 * 8/2006 Lehrman et al. ............ 340/669

* cited by examiner

*Primary Examiner*—Benjamin C. Lee
*Assistant Examiner*—Travis R. Hunnings
(74) *Attorney, Agent, or Firm*—Ingrassia Fisher & Lorenz

(57) ABSTRACT

A system and method is provided for detection of a human body fall event. The fall detection system (100, 200) includes a monitoring unit (102, 202), including a plurality of accelerometers (106, 206), a processor (108, 208) and a wireless transmitter (110, 210). The plurality of accelerometers (106, 206) provide acceleration measurements to the processor (108, 208), the measurements describing the current acceleration of the person wearing the monitoring unit (102, 202) in all directions. The processor (108, 208) receives the acceleration measurements and compares the acceleration measurements to a value range to determine if the wearer is currently experiencing a fall event. The processor (108, 208) generates a signal in response to the detection of a fall event and the transmitter (110, 210) transmits the signal to a remote signal receiver (104, 204). The system and method can further detect non-movement in the wearer of the monitoring unit (102, 202) subsequent to the fall event to detect an unconscious wearer.

16 Claims, 4 Drawing Sheets

SYSTEM AND METHOD FOR HUMAN BODY FALL DETECTION

FIELD OF THE INVENTION

This present invention generally relates to the field of human monitoring devices, and more particularly to an improved monitoring device that detects falls of a human body and movement of the human body subsequent to the fall.

BACKGROUND OF THE INVENTION

Falls in individuals are recognized as a major health and welfare issue in the elderly, infirmed, or disabled population and with regard to community helpers, such as firefighters, police, or the like. Monitoring falls in the elderly has been recognized as a growing problem due in part to our aging population. In many instances, continuous monitoring of these individuals is necessary to render aid when needed, and prevent further major health issues that result from a fall. Research has shown there is a direct correlation between major health issues and the amount of time an individual remains in a fall position. Current monitoring devices for the elderly, infirmed, or disabled are typically in the form of a device that requires user input, such as push button activation, to alert the monitor that a fall event or other emergency has occurred. The problem with this type of monitoring device is that many times the individual being monitored is not in a condition to activate the control, such as when a fall has occurred and the individual is rendered unconscious.

In addition, monitoring of police and firefighters when entering dangerous situations, is needed. Similar to falls in the elderly, infirmed or disabled, falls by firefighters and police when in danger require monitoring without user input to activate an alarm. For example, many instances of falls of firefighters occur when entering a building and the firefighter is overwhelmed by smoke due to smoke inhalation that results in unconsciousness. A firefighter might fall when struck by falling debris. In addition, falls from ladders, etc. and subsequent injury may occur where no one else is present at the time of the fall. As stated above, the activation of a monitoring device, such as pushing a button, requires the fallen individual to be conscious. As was the case previously, this requirement presents a problem when the fallen individual is unconscious or otherwise unable to activate the device.

Detecting the occurrence of falls and the status of the individual post-fall is needed in a device that is accurate and convenient. Unfortunately, prior methods for detecting a fall have required the individual seeking help to activate a control that submits an alert to the monitoring person or entity. Thus, what is needed is an improved system and method for detecting when a person falls down that is reliable and efficient and does not require user activation.

BRIEF DESCRIPTION OF DRAWINGS

The present invention will hereinafter be described in conjunction with the following drawing figures, wherein like numerals denote like elements.

DETAILED DESCRIPTION OF THE INVENTION

The present invention provides a system and method for fall detection of a human body through recognition of a fall signature. The system and method provides the ability to reliably detect falls and subsequent movement of the person to determine post-fall condition. Human body fall signatures can be categorized as linear, or non-linear in nature. A linear fall signature occurs when a fall results without significant movement or outside force being applied. A linear fall signature would occur when an individual falls through a void or hole, as for example when a floor gives way beneath, or if they collapse straight down such as in a situation with police or a firefighter during a fire. A non-linear fall signature would occur when an individual falls with significant rotation of the body or when the fall is accompanied by additional external force, such as where one falls as a result of being struck by an object.

Figure 1:
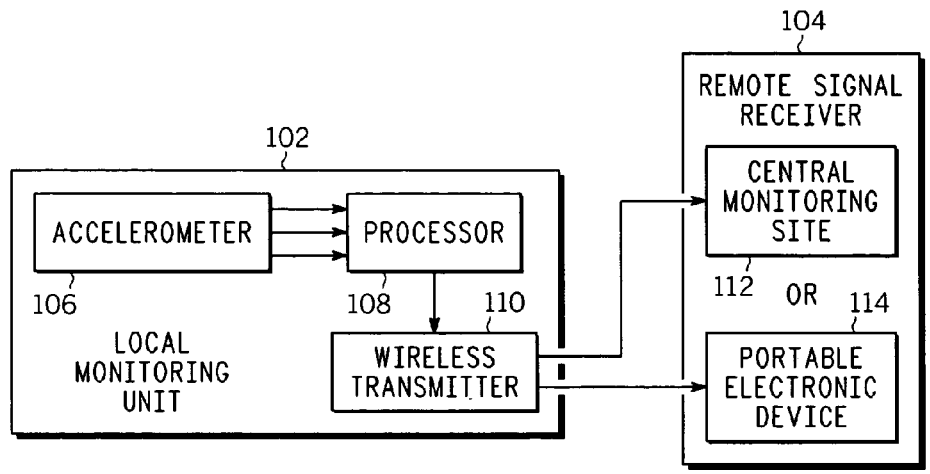
FIG. 1 is a schematic view of a fall detection system in accordance with a first embodiment of the invention.

Turning now to the drawings, FIG. 1 illustrates in schematic view a fall detection system 100 according to a first embodiment of the present invention. Fall detection system 100 includes a local monitoring unit 102 and a remote signal receiver 104. Local monitoring unit 102 comprises a plurality of accelerometers 106, a processor 108 having inputs coupled to accelerometer 106, and a transmitter for wirelessly transmitting a signal to remote signal receiver 104, such as a wireless transmitter 110 coupled to processor 108. The plurality of accelerometers 106 provide acceleration measurements to processor 108, representative of the current acceleration in all directions of the person wearing local monitoring unit 102.

To provide for fall detection, accelerometers 106 are worn where they can sense the acceleration of the wearer during a fall event. The term "fall event" as used herein is defined as an event that results in a person coming to rest inadvertently on the ground or other lower level. To detect a linear fall signature, processor 108 receives the acceleration measurements and compares the acceleration measurements to a value range. To detect a non-linear fall signature, processor 108 compares combinations of acceleration measurements to a value range and further determines the smoothness of the acceleration measurement combinations. If the acceleration measurement combinations are within the value range and do not fall within a smoothness value range, then a non-linear fall event is occurring.

When a fall is detected, processor 108 provides a fall detection signal to remote signal receiver 104. Remote signal receiver 104 is either a remotely located central monitoring site 112 or a portable receiving device 114. Central monitoring site 112 comprises a remote site that is configured to receive wirelessly transmitted fall detection signals from local monitoring unit 102. Portable receiving device 114, and more specifically a phone or paging device, is configured to receive wirelessly transmitted fall detection signals from local monitoring unit 102 and is designed to be worn by a person who is to be alerted if a fall event occurs.

As stated, system 100 can reliably detect a linear fall, or the more common non-linear fall, such as when the wearer's fall is accompanied with rotation or is initiated by additional external force. During operation, processor 108 receives the acceleration measurements from accelerometer 106 and compares the acceleration measurements to a value range to determine if the person is experiencing a fall event. Subsequent to the detection of a fall event, processor 108 additionally compares further acceleration measurements to a value range stored in processor 108 and determines whether the acceleration measurements are within the value range to identify no additional movement or minimal movement of the wearer subsequent to the fall event. If the acceleration measurement combinations are within the value range and no movement or minimal movement is detected, then the wearer may not be conscious and emergency measures can be initiated. If the acceleration measurement combinations are not within the value range and movement is detected, then the monitoring service or individual is notified a fall event has occurred and emergency aid can be dispatched. Alternatively, the wearer can contact remote signal receiver 104, and specifically the monitoring service in the case of an emergency, or lack thereof, and take appropriate measures.

When a fall event is detected, processor 108 provides a fall detection signal to wireless transmitter 110. In this first embodiment, wireless transmitter 110 then transmits a signal directly to remote signal receiver 104, and more specifically to central monitoring site 112, to portable receiving device 114, or both.

Figure 2:
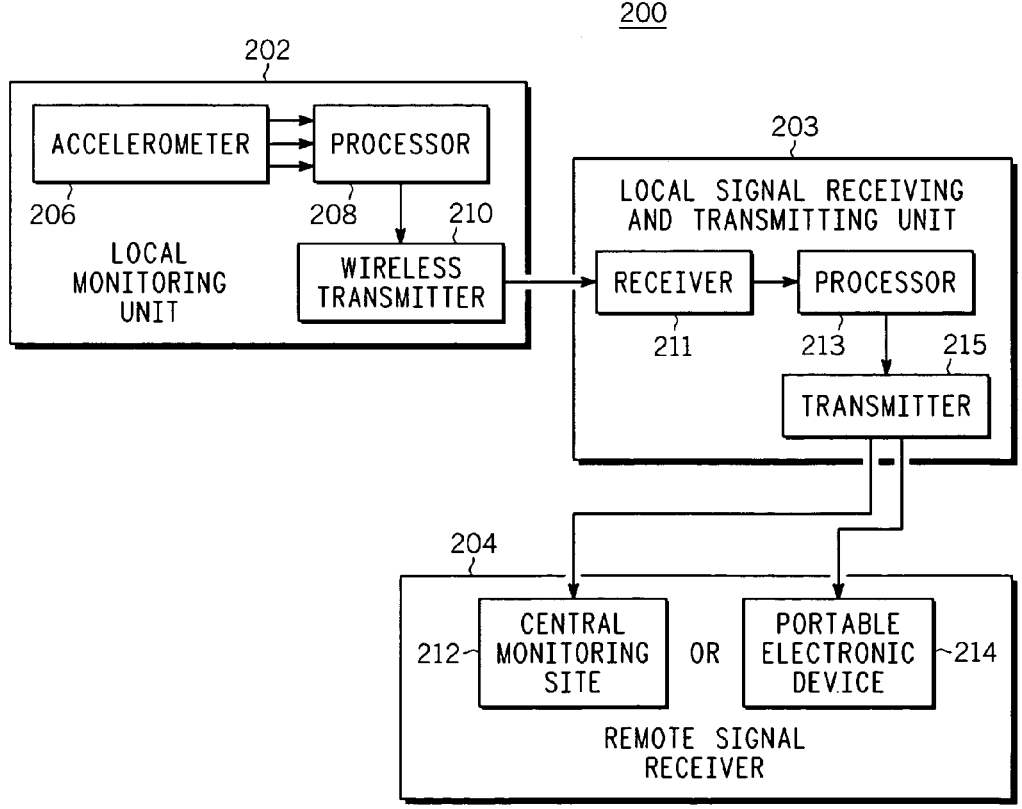
FIG. 2 is a schematic view of a fall detection system in accordance with a second embodiment of the invention.

FIG. 2 illustrates in schematic view a fall detection system 200 according to a second embodiment of the present invention. Fall detection system 200 includes a local monitoring unit 202, a local signal receiving and transmitting unit 203, and a remote signal receiver 204. Fall detection system 200, and more specifically local monitoring unit 202, includes a plurality of accelerometers 206, a processor 208 having inputs coupled to accelerometer 206, and a wireless transmitter 210 coupled to processor 208, for transmitting a fall detection signal to local signal receiving and transmitting unit 203. Local signal receiving and transmitting unit 203 receives the fall detection signal, and further generates an alert signal for transmission to remote signal receiver 204. Local signal receiving and transmitting unit 203 is intended to be positioned in the same general area as local monitoring unit 202, such as in the home of an elderly wearer of local monitoring unit 202. Local signal receiving and transmitting unit 203 comprises a receiver 211 for receiving wireless transmissions from local monitoring unit 202, a processor 213 for generating an alert signal, and a transmitter 215. In contrast to the first embodiment, this embodiment provides for wired or wireless transmission of an alert signal to remote signal receiver 204 via transmitter 215.

Remote signal receiver 204 comprises a remotely located central monitoring site 212 and/or a portable receiving device 214, such as a phone or paging device. Central monitoring site 212 is configured to receive transmitted signals from local signal receiving and transmitting unit 203. Portable receiving device 214 is likewise configured to receive transmitted signals from local signal receiving and transmitting unit 203 and can be worn by a person monitoring potential fall events. In this embodiment, a fall detection signal is generated by processor 208 and wirelessly transmitted by transmitter 215 to local signal receiving and transmitting unit 203 that in turn, receives and processes the fall detector signal and subsequently transmits an alert signal to remote signal receiver 204 via wired or wireless transmission.

During operation, the plurality of accelerometers 206 provide acceleration measurements to processor 208. These measurements describe the current acceleration in all directions of the person wearing monitoring unit 202. To provide for fall detection, accelerometers 206 are configured on the wearer where they can sense the acceleration of the wearer during a fall event. Processor 208 receives the acceleration measurements and compares the acceleration measurements to a value range to determine if the person is experiencing a fall event.

System 200 can reliably detect a linear fall signature or a non-linear fall signature. During operation, processor 208 receives the acceleration measurements and compares the acceleration measurements to a value range to determine if the person is experiencing a fall event. Subsequent to the detection of a fall event, processor 208 additionally compares further acceleration measurements to a value range stored in processor 208 and determines whether the acceleration measurements are within the value range to identify lack of movement, or minimal movement subsequent to the fall event. If the acceleration measurement combinations are within the value range and no movement or limited movement is detected, then the wearer may not be conscious and emergency measures can be taken.

When a fall is detected, processor 208 provides a fall detection signal to transmitting device 210, such as a wireless transmitting component. In this second embodiment, transmitting device 210 wirelessly transmits a signal to a local signal receiving and transmitting unit 203, and ultimately unit 203 transmits an alert signal to either central monitoring site 212 or to portable phone or paging device 214.

The present invention can be used to detect falls in a wide variety of instances. For example, it can be used to detect falls of the elderly, infirmed, or disabled. Upon the detection of a fall event, the central monitoring system would be alerted to send help. In addition, the detection of non-movement can be detected where the wearer is unconscious and not able to respond to the central monitor system. It can also be used to detect falls of community helpers, such as firefighters, police officers, or other individuals who are placed in harm's way. More particularly, the device can be used by those entering burning buildings and monitored by individuals remaining outside, to determine when a fall event occurs. In all these events, the present invention can be adapted to detect a fall, determine current state of consciousness via movement of the wearer, and provide a signal to a central monitoring system or portable device regarding the detected event.

A variety of different types of accelerometers can be used in the system and method. One specific type of accelerometer that can be used is a micromachined accelerometer. For example, micromachined accelerometers can be used to accurately measure acceleration using changes in capacitance. Capacitive micromachined accelerometers offer high sensitivity with low noise and low power consumption and thus are ideal for many applications. These accelerometers typically use surface micromachined capacitive sensing cells formed from semiconductor materials. Each cell includes two back-to-back capacitors with a center plate between the two outer plates. The center plate moves slightly in response to acceleration that is perpendicular to the plates. The movement of the center plate cause the distance between the plates to change. Because capacitance is proportional to the distance between plates, this change in distance between plates changes the capacitance of the two capacitors. This change in capacitance of the two capacitors is measured and used to determine the acceleration in the direction perpendicular to the plates, where the direction perpendicular to the plates is commonly referred to as the axis of the accelerometer.

Typically, micromachined accelerometers are packaged together with an application specific integrated circuit (ASIC) that measures the capacitance, extracts the acceleration data from the difference between the two capacitors in the cell, and provides a signal that is proportional to the acceleration. In some implementations, more than one accelerometer will be combined together in one package. For example, some implementations include three accelerometers, with each accelerometer is configure to measure acceleration in a different orthogonal axis. The three accelerometers are designed or packaged together with the ASIC used to measure and provide the acceleration signals for all three directions. Other implementations are packaged with one accelerometer per device or two accelerometers per device. All of these implementations can be adapted for use in the fall detection system and method.

One suitable accelerometer that can be adapted for use in the system and method is a triple-axis accelerometer MMA7260Q available from Freescale Semiconductor, Inc. This accelerometer provides the advantage of measuring acceleration in all three directions with a single package. Other suitable accelerometers include dual axis accelerometer MMA6260Q and single axis accelerometer MMA1260D. Other types of accelerometers that can be used include a combination of MMA6161Q, MMA6262Q, MMA6263Q, and MMA2260D with the MMA1260D or by mounting a device on its side to achieve 3-axis sensing. Of course, these are just some examples of the type of accelerometers that can be used in the fall detection system and method.

Figure 3:
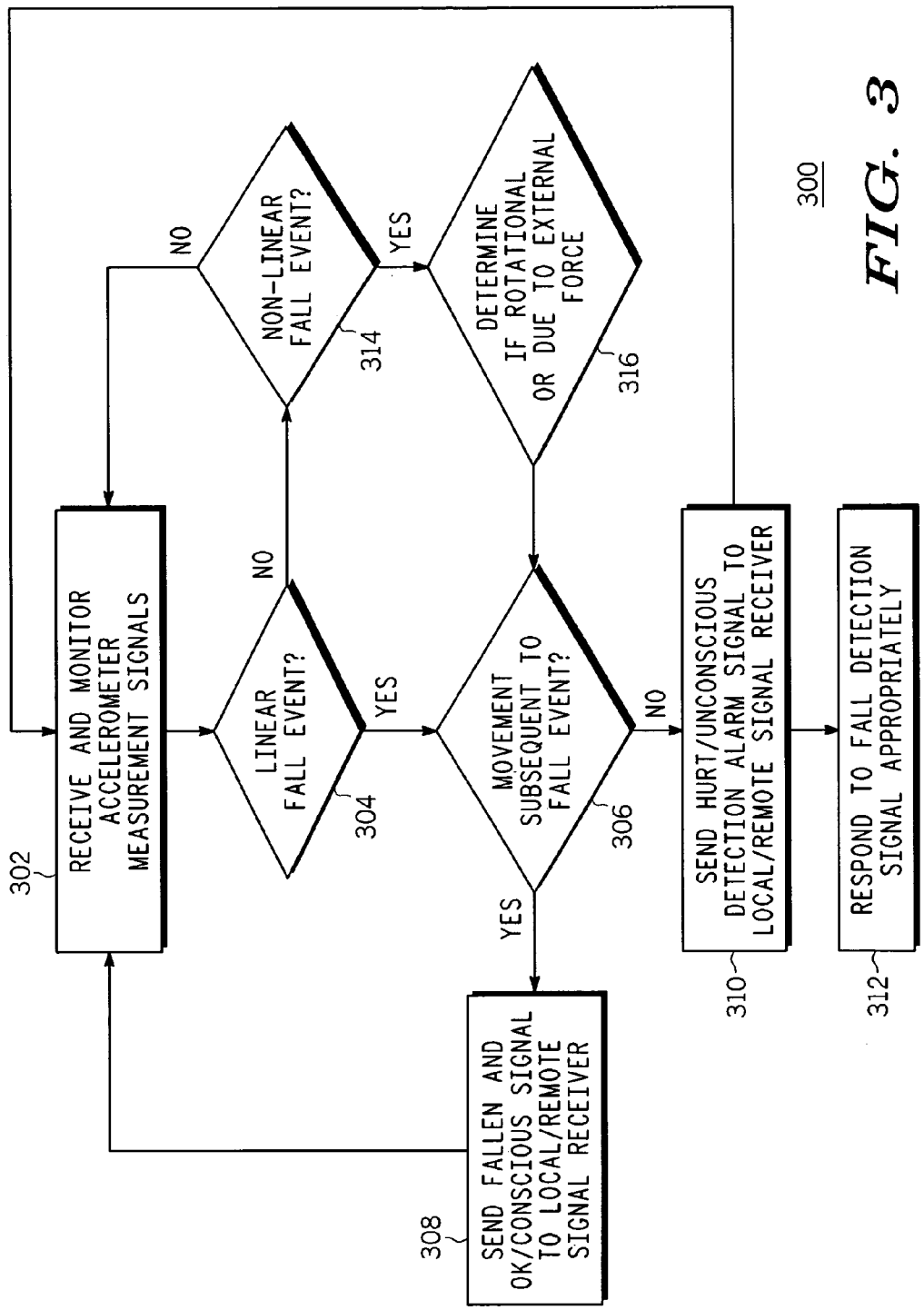
FIG. 3 is a flow diagram of a fall detection method in accordance with an embodiment of the invention.

FIG. 3 illustrates a method 300 of fall detection according to the present invention. Method 300 provides for the ability to detect a fall event by a wearer of a monitoring device, such as that described in FIGS. 1 and 2. Method 300 tests for both linear fall signatures and non-linear fall signatures. Detecting non-linear fall signatures is generally more complex due to the other actions operating on the device during the fall. Thus, method 300 first searches for linear fall signatures before searching for non-linear fall signatures.

First, accelerometer measurement signals are received (302). Typically the accelerometer measurement signals are provided by at least three accelerometers, where the at least three accelerometers are configured to measure acceleration in three orthogonal axes. Thus, there is at least one accelerometer measuring acceleration in an X-axis, at least one accelerometer measuring acceleration in a Y-axis, and at least one accelerometer measuring acceleration in a Z-axis, where X, Y and Z are orthogonal axes. Of course, different arrangements of accelerometers could be used in some embodiments.

With the accelerometer measurement signals received, the next step (304) is to determine if a linear fall signature is occurring. As will be described in detail below, one method of determining if a linear fall is occurring is to compare the measurement signals to a value range. If the measurement signals for each axis are each within a specified value range for a specified number of measurements, then a linear fall is determined to be occurring.

When it is determined that the fall is a linear fall, it next determines if there is any movement subsequent to the fall event (306). One method of making this determination is by comparing additional measurement signals to a value range. If the measurement signals for each axis are each within a specified value range for a specified number of measurements, then movement subsequent to the fall is detected and the next step 308 is to submit a signal to the remote signal receiver that the wearer of the monitoring unit has experienced a fall event, but appears to be conscious. If there is no subsequent movement detected, a fall detection signal is transmitted to the remote signal receiver (step 310). Appropriate action can then be taken to assist the person wearing the monitoring unit (step 312).

If the fall is not linear, the next step 314 is to determine if the fall signature corresponds to a non-linear fall. As will be described in detail below, one method of determining if the fall is a non-linear fall, is by comparing combinations of acceleration measurements to a value range. Smoothness of the fall is also determined. If the acceleration measurement combinations are within the value range and not smooth, then a non-linear fall condition is occurring. As will be described below, one exemplary combination of measurements that can be used is a sum of the squares of the measurements.

After it has been determined that a non-linear fall is occurring, it is next determined if the fall is a rotational fall or a fall due to an external force (step 316). For example, the system and method can be adapted to determine if the fall was the result of being struck by falling debris. To determine if the fall was initiated by an external force, the previously sampled data points that were read before the fall occurred are analyzed to determine if the device experienced high accelerations in one or more directions. If such acceleration was present during the predetermined period before the fall, it can be assumed that the fall was initiated by external force, e.g., struck by falling debris.

After it has been determined that a non-linear fall has occurred, it must next be determined if there is any movement subsequent to the fall, as previously described (step 306) If no movement is detected, a fall detection signal is sent to the remote signal receiver (step 310).

The method then returns to step 302 where data is continuously received and evaluated to determine if a fall event is occurring. It should be noted that the steps in method 300 are merely exemplary, and that other combinations of steps or orders of steps can be used to provide fall detection. For instance, a fall detection signal can be transmitted to the remote signal receiver irrespective of whether movement subsequent to the fall event is detected.

Figure 4:
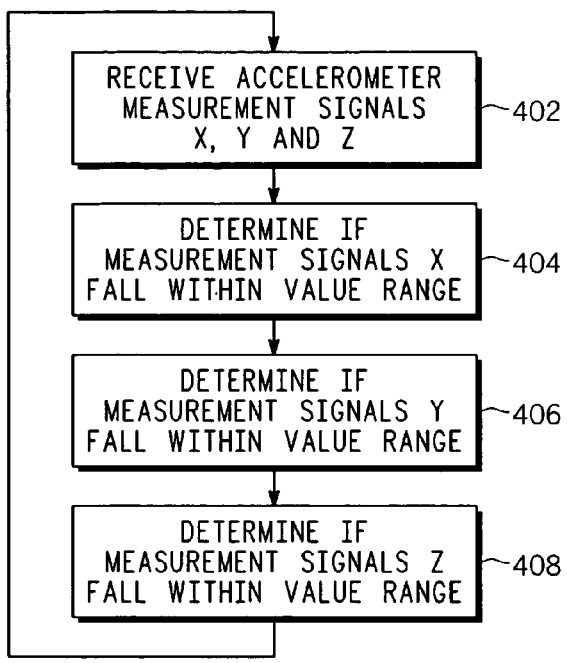
FIG. 4 is a flow diagram of a linear fall detection method in accordance with an embodiment of the invention.

FIG. 4 illustrates a method 400 for detecting a linear fall signature. The method 400 can be used to implement step 304 in method 300 (FIG. 3). The method 400 is based on the observation that a body having a linear fall signature will have acceleration measurements in all directions go toward a value that corresponds to zero g acceleration. Thus, the method 400 compares measurements from each accelerometer to a selected value range, with the value range defining a set of acceleration values around zero g. The value range used would depend on a variety of factors. Typically, the larger the value range, the more likely a fall will be detected when it occurs. However, a larger value range will also increase the likelihood that non-fall conditions are erroneously determined to be falls. It should be noted that because this method compares the acceleration to a value range around zero g that some relatively low-end accelerometers with low effective measurement ranges can be used to provide the acceleration measurements and that expensive calibration can also be avoided.

In the first step 402, accelerometer measurement signals x, y and z are received, with the signals corresponding to measurements in X, Y and Z orthogonal directions. The format of the measurement signals would typically depend on the accelerometer used and how the output of the accelerometer is processed. Typical accelerometers provide a voltage that is proportional to the acceleration as an output. This output voltage can then be converted to a digital representation using an appropriate analog-to-digital converter. The conversion can be done by the processor, by the ASIC associated with accelerometers, or with separate converters. The number of bits used to represent the output would typically depend on a variety of factors, such as the desired resolution and the cost of components. As one example, an 8-bit solution can be used that would provide a range of 256 possible acceleration values, with a value of 128 corresponding to zero g. This nominal offset voltage provides for the accelerometer to detect both positive and negative acceleration. Additionally, the rate at which the analog-to-digital conversion is performed would depend upon the speed of the various components. For example, a typical suitable converter would provide digital values from the analog signals at a rate of 200 Hz.

In the next step (404) it is determined if measurement signals x fall within a value range. As stated above, the value range defines a margin of acceleration values around zero g. One exemplary value range covers within plus/minus four percent of zero g. In an 8-bit solution, this would correspond to acceleration values of within plus/minus 5 bits of one hundred twenty eight. Of course, this is just one example of a value range that can be used.

Likewise, it is next determined if measurement signals y fall within the value range (step 406), and next it is determined if the measurements signals z fall within the value range (step 408).

Typically, steps 404, 406 and 408 would be implemented such that a linear fall signature is detected only when measurement signals x, y and z are determined to be within the value range for a selected period of time. Requiring that each signal x, y and z be in the value range for a predetermined time period reduces the probability that random movements that result in near zero g measurement signals will be misinterpreted as indicative of a fall event. As one example, steps 404, 406 and 408 can be implemented such that the signals are determined to fall within the value range when the signals are within the value range for at least 1/20 of a second. In a system where digital measurement signals are provided at 200 Hz, a fall condition would thus be determined when ten consecutive measurements are within the value range for each axis simultaneously. Such an implementation facilitates relatively fast fall detection while reducing the likelihood of erroneous fall detections.

Steps 402–408 of method 400 would be performed in real time, with the processor continually receiving measurement signals and determining if the past sets of measurement signals have been within the value range for a predetermined time period. This can be accomplished by continually loading the measurements into an appropriate FIFO buffer and evaluating the contents of the buffer to determine if the criteria are met for each set of measurement signals, then loading the next set of measurements, and removing the oldest set of measurements.

Figure 5:
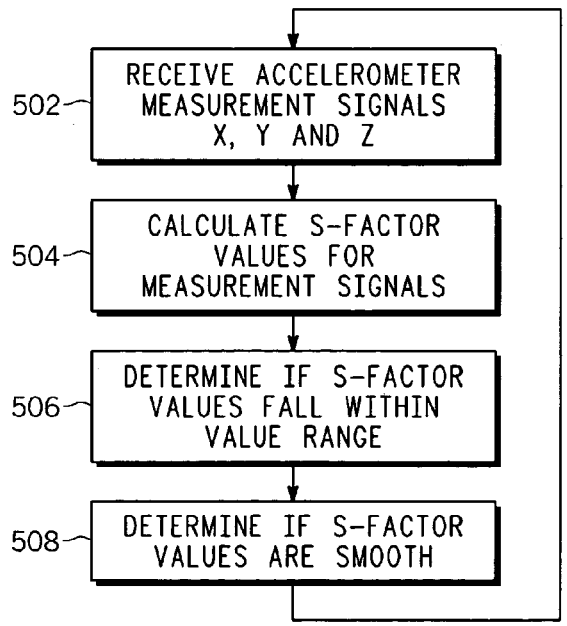
FIG. 5 is a flow diagram of a non-linear fall detection method in accordance with an embodiment of the invention.

Turning now to FIG. 5, a method 500 for detecting a non-linear fall signature is illustrated. The method 500 can be used to implement step 306 in method 300 (FIG. 3). The method 500 is based on the observation that a non-linear falling body signature will have certain combinations of acceleration measurements go toward a value that corresponds to zero g acceleration. Thus, the method 500 compares combinations of measurements from each accelerometer to a selected value range, with the value range defining a combination of acceleration values around zero g. The method 500 then determines the smoothness of the combination of acceleration values, generally referred to herein as $S_{factor}$ values, and determines if they are within the value range.

In the first step, accelerometer measurement signals x, y and z are received with the signals corresponding to measurements in X, Y and Z orthogonal directions (step 502). Again, the format of the measurement signals would typically depend on the accelerometer used and how the output of the accelerometer is processed. For example, an 8-bit solution can again be used that provides digital measurement values at a rate of 200 Hz.

The next step (504) is to calculate the $S_{factor}$ values from the measurement signals. In general, the $S_{factor}$ is defined and calculated to provide a combination of measurement values that is a good indication of non-linear falling body, such as to what degree external influence is acting upon it, such as falling debris. A variety of types of combinations can be used. One exemplary $S_{factor}$ combination can be defined as:

$$S_{Factor} = x^2 + y^2 + z^2$$

where x, y and z are the acceleration measurement signals. In this equation, the $S_{factor}$ combination is defined as the sum of the squares of the measurement signals, where the measurement signals are in g's (e.g., x=(x1−xoffset)÷sensitivity). Of course, other equations and calculations can be used to define and calculate the $S_{factor}$. Thus in step 504, a combination of measurement values called $S_{factor}$ values are calculated that can be used to determine if a non-linear fall signature exists or to what degree external influence is acting upon the body falling.

In the next step (506), it is determined if the combinations of measurement signals $S_{factor}$ are within a specified value range. Again, the value range defines a margin of $S_{factor}$ values around zero g. One exemplary value range is to select a range that covers within +/3 to 12 percent of zero g. In an exemplary 8-bit solution, this would correspond to $S_{factor}$ values of within +/−2 to 7 bits of 128. Of course, this is just one example of a value range that can be used.

Next, it is determined if the combination of measurement signals $S_{factor}$ are smooth (step 508). The smoothness of the $S_{factor}$ values can be calculated by determining the amount of change between consecutive $S_{factor}$ values and comparing the amount of change to a threshold delta value. The threshold delta value used would again depend on a variety of factors. In an 8-bit solution, the threshold delta value can be +/−2 to 7 bits. Thus, if consecutive $S_{factor}$ values are within +/−2 to 7 bits then the $S_{factor}$ is smooth at that time.

Typically, steps 506 and 508 would be implemented such that a non-linear fall signature is detected only when the $S_{factor}$ values are determined to be within the value range and smooth for a selected period of time. Requiring the $S_{factor}$ values to be in the value range and smooth for a predetermined time period reduces the probability that random movements will be misinterpreted as indicative of a non-linear fall condition. As one example, steps 506 and 508 can be implemented such that the $S_{factor}$ values are determined to be indicative of a non-linear fall when they are within the value range and be smooth for at least 50 to 150 milliseconds. In a system where digital measurement signals are provide at 200 Hz, a non-linear fall condition would thus be determined when ten consecutive measurements result in $S_{factor}$ values that are within the value range and are smooth. Such an implementation facilitates relatively fast fall detection while reducing the likelihood of erroneous fall detections.

Steps 502–508 of method 500 would be performed in real time, with the processor continually receiving measurement signals and determining if the past sets of measurement signals have $S_{factor}$ values that are within the value range and smooth. This can be accomplished by continually loading the measurements into an appropriate FIFO buffer and evaluating the contents of the buffer to determine if the criteria are met for resulting $S_{factor}$ values, then loading the next set of measurements and removing the oldest set of measurements.

Figure 6:
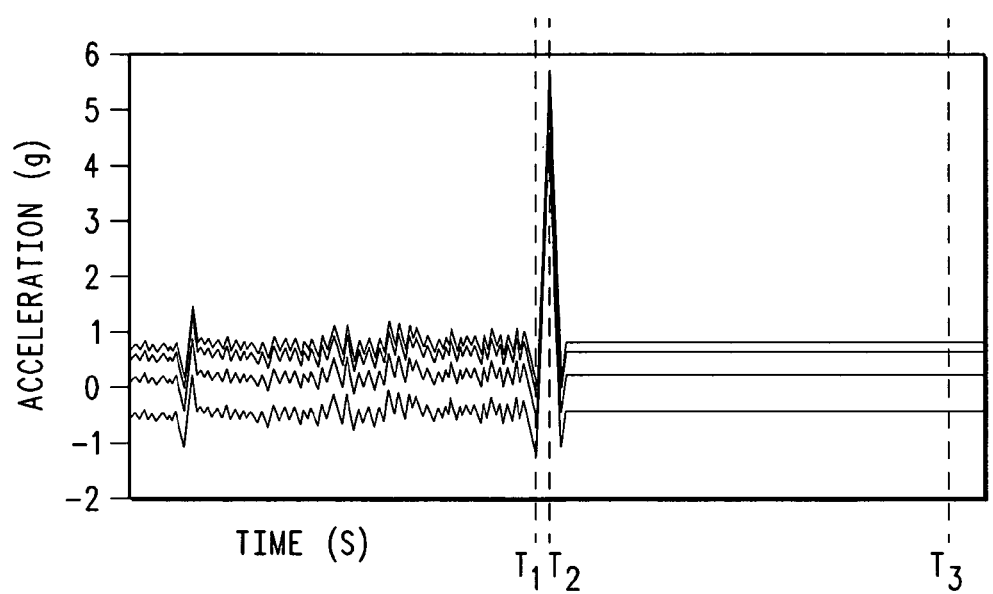
FIG. 6 is a graph of exemplary acceleration measurements during fall conditions in accordance with an embodiment of the invention.

FIG. 6 is a graph 600 of exemplary accelerometer measurement signals x, y and z taken over a time period during which a fall event occurs. Graph 600 illustrates a fall condition occurring at time $T_1$. As illustrated in graph 600, at time $T_1$ the measurement signals x, y and z all are within a value range of zero g. Thus, a fall event is detected when the signals x, y and z are simultaneously within the value range for a predetermined time period. At time $T_2$, the signals leave the value range, thus indicating the resulting impact shock. The amount of time between $T_1$ and $T_2$ is the approximate fall time. If necessary, this fall time can be used to calculate the fall distance. Specifically, the fall distance will be approximately equal to the total number of time segments that the individual wearing the monitoring unit is in freefall multiplied by the seconds per time segment, also known as the sample time. For the 200 Hz example, this multiplication factor would be 60/200=0.3 seconds per time segment. Measurements taken between $T_1$ and $T_3$ note no movement of the wearer, thus indicating the wearer of the monitoring device is unconscious.

The fall detection system can be implemented with a variety of different types and configurations of devices. As discussed above, the system is implemented with a processor that performs the computation and control functions of the fall detector. The processor may comprise any suitable type of processing device, including single integrated circuits such as a microprocessor, or combinations of devices working in cooperation to accomplish the functions of a processing unit. In addition, the processor may part of the electronic device's core system or a device separate to the core system. Furthermore, it should be noted that in some cases it will be desirable to integrate the processor functions with the accelerometers. For example, a suitable state machine or other control circuitry integrated with the accelerometers can implement the plurality of accelerometers and the processor in a single device solution. In such a system circuitry can be used to directly determine if the accelerometer plates are close to a zero position, and provide the warning to the device.

The processor can comprise special purpose hardware configured for fault detection. Alternatively, the processor can comprise a programmable processor that executes programs stored in a suitable memory, with the programs configured to provide fault detection. Thus, those skilled in the art will recognize that the mechanisms of the present invention are capable of being distributed as' a program product in a variety of forms, and that the present invention applies equally regardless of the particular type of signal bearing media used to carry out the distribution. Examples of signal bearing media include: recordable media such as floppy disks, hard drives, memory cards and optical disks, and transmission media such as digital and analog communication links, including wireless communication links.

The present invention thus provides a system for determining if a human body has fallen, the system comprising: a local monitoring unit and a remote signal receiver comprising one of a central monitoring site or a portable electronic device. The local monitoring unit includes a plurality of accelerometers, a processor and a wireless transmitter. The plurality of accelerometers can be micro machined accelerometers. The plurality of accelerometers measure acceleration of a human body in a plurality of directions and produce a plurality of acceleration measurements. The processor receives the plurality of acceleration measurements from the plurality of accelerometers, compares them to a value range and generates a signal if the plurality of acceleration measurements are within the value range indicating a fall event has occurred. The wireless transmitter transmits the signal to a remote signal receiver. The processor can determine if the plurality of acceleration measurements are within the value range for a predetermined number of consecutive acceleration measurements. The processor can further determine if a non-linear fall is occurring by determining if the plurality of acceleration measurements has smoothness with a specified range by determining if a selected number of consecutive acceleration measurements each has a change less than a threshold delta value.

The plurality of accelerometers includes a first accelerometer providing a first acceleration measurement x, a second accelerometer providing a second acceleration measurement y, and a third accelerometer providing a third acceleration measurement z. During operation, the processor determines if the plurality of acceleration measurements has smoothness within a specified range by determining if $x^2+y^2+z^2$ has a change less than a threshold delta value for a selected number of consecutive acceleration measurements. The processor further determines if a detected fall event was accompanied by external force by determining if a combination of the acceleration measurements exceeded a threshold value in a time period prior to the detected fall event.

The present invention further provides for a system for determining if a human body is falling, wherein the system comprises a local monitoring unit including a first accelerometer providing a first acceleration measurements x, a second accelerometer providing a second acceleration measurements y, and a third accelerometer providing a third acceleration measurements z. A local monitoring unit further includes a processor for receiving the first acceleration measurements x, the second acceleration measurements y, and the third acceleration measurements z. The processor compares the measurements to a value range, and determines whether a fall event is occurring and generates a signal in response to the detected fall event that is wirelessly transmitted to the remote signal receiver. The system can further include a local signal receiving and transmitting unit for receiving the wireless signal generated by the local monitoring unit, and transmitting the signal to the remote signal receiver. The system can determine if movement subsequent to the fall event is present by receiving a plurality of acceleration measurements from the plurality of accelerometers subsequent to the fall event. The system compares the plurality of acceleration measurements to a value range and generates a signal if the plurality of acceleration measurements are within the value range indicating movement subsequent to the fall event.

The present invention further provides for a method for determining if human body is falling, wherein the method comprises the steps of measuring acceleration of a human body wearing a monitoring unit in a plurality of directions and producing a plurality of acceleration measurements. The plurality acceleration measurements are compared to a value range to determine if they are within the value range indicating a fall event has occurred. A signal is in response to the fall event and transmitted to a remote signal receiver.

The plurality of acceleration measurements include a first acceleration measurement x, a second acceleration measurement y, and a third acceleration measurement z. The accelerometers are micromachined accelerometers. The plurality of acceleration measurements are received from a first accelerometer measuring acceleration in a X direction, a second accelerometer measuring acceleration in a Y direction, and a third accelerometer measuring acceleration in a Z direction, where X, Y and Z are perpendicular to each other.

The processor compares the first acceleration measurements x, the second acceleration measurements y, and the third acceleration measurements z to a value range. If the first acceleration measurements x, the second acceleration measurements y, and the third acceleration measurements z are each within the value range for a first selected number of measurements, it determines a fall event is occurring. The processor can further combine the first acceleration measurements x, the second acceleration measurements y, and the third acceleration measurements z into a combination of $x^2+y^2+z^2$ values and compare the combination of $x^2+y^2+z^2$ values to a second value range, to determine if the combination of $x^2+y^2+z^2$ values has an amount of change less than a threshold delta value for a second selected number of measurements. This measurement will aid in determining if a detected fall was accompanied by external force by determining if a combination of the acceleration measurements exceeded a threshold value in a time period prior to the detected fall.

The embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed. Many modifications and variations are possible in light of the above teaching without departing from the spirit of the forthcoming claims.

The invention claimed is:

1. A system for determining if a body has fallen, the system comprising:
 a local monitoring unit, the local monitoring unit comprising:
  a plurality of accelerometers configured to measure the acceleration of the body in a plurality of directions and produce a plurality of acceleration measurements; and
  a processor configured to: (i) receive the plurality of acceleration measurements, and (ii) emit a fall detection signal when the smoothness of the plurality of acceleration measurements to determine smoothness is within a specified range; and
 a remote signal receiver configured to receive the fall detection signal.

2. A system for determining if a body has fallen as claimed in claim 1 wherein the local monitoring unit further comprises a wireless transmitter for transmitting the fall detection signal to the remote signal receiver.

3. A system for determining if a body has fallen as claimed in claim 1 wherein the remote signal receiver is one of a central monitoring site or a portable electronic device.

4. A system for determining if a body has fallen as claimed in claim 1 wherein the plurality of accelerometers comprise a first accelerometer providing a first acceleration measurement x, a second accelerometer providing a second acceleration measurement y, and a third accelerometer providing a third acceleration measurement z, and wherein the processor determines if the plurality of acceleration measurements has smoothness within a specified range by determining if $x^2+y^2+z^2$ has a change less than a threshold delta value for a selected number of consecutive acceleration measurements.

5. A system for determining if a body has fallen as claimed in claim 1 wherein the plurality of accelerometers comprise a first accelerometer measuring acceleration in a X direction, a second accelerometer measuring acceleration in a Y direction, and a third accelerometer measuring acceleration in a Z direction, where X, Y and Z are perpendicular to each other.

6. A system for determining if a body has fallen as claimed in claim 1 wherein the processor further determines if a detected fall event was accompanied by external force by determining if a combination of the acceleration measurements exceeded a threshold value in a time period prior to the detected fall event.

7. A system for determining if a body is falling, the system comprising:
 a local monitoring unit, the local monitoring unit comprising:
  an accelerometer assembly attached to the body for generating signals representative of the body's acceleration, the accelerometer assembly comprising at least one accelerometer measuring acceleration of a body in at least one direction,
  a processor configured to: (i) determine an $S_{factor}$ value from the signals generated by the accelerometer assembly, the $S_{factor}$ value indicative of a smoothness of acceleration; and (ii) emit a fall detection signal when the $S_{factor}$ value falls within a predetermined range; and
 a remote signal receiver comprising one of a central monitoring site or a portable electronic device, the remote signal receiver receiving the fall detection signal generated by the processor in response to the fall event.

8. A system for determining if a body is falling as claimed in claim 7 wherein the local monitoring unit includes a first accelerometer providing a first acceleration measurements x, a second accelerometer providing a second acceleration measurements y, and a third accelerometer providing a third acceleration measurements z.

9. A system for determining if a body is falling as claimed in claim 8 further including a local signal receiving and transmitting unit for receiving the wireless signal generated by the local monitoring unit, and transmitting the signal to the remote signal receiver.

10. A method for determining if a body wearing a monitoring unit is falling, the method comprising:
 measuring acceleration of the body in a plurality of directions and producing a plurality of acceleration measurements;
 determining an $S_{factor}$ value from the plurality of acceleration measurements, the $S_{factor}$ value indicative of a smoothness of the acceleration measurements;

comparing the determined $S_{factor}$ value to a value range indicating a fall event has occurred;

generating a signal when the determine $S_{factor}$ value falls within the value range; and transmitting the signal to a remote signal receiver.

11. A method for determining if a body is falling as claimed in claim 10 wherein the plurality acceleration measurement comprises a first acceleration measurement x, a second acceleration measurement y, and a third acceleration measurement z.

12. A method for determining if a body is falling as claimed in claim 10 wherein the plurality acceleration measurements are received from a plurality of micro machined accelerometers.

13. A method for determining if a body is falling as claimed in claim 10 wherein the plurality acceleration measurements are received from the plurality of accelerometers that comprise a first accelerometer measuring acceleration in a X direction, a second accelerometer measuring acceleration in a Y direction, and a third accelerometer measuring acceleration in a Z direction, where X, Y and Z are perpendicular to each other.

14. A method for determining if a body is falling as claimed in claim 13 further including the step of comparing the first acceleration measurements x, the second acceleration measurements y, and the third acceleration measurements z to a value range, wherein a fall is determined to be occurring if the first acceleration measurements x, the second acceleration measurements y, and the third acceleration measurements z are each within the value range for a first selected number of measurements.

15. A method for determining if a body is falling as claimed in claim 14 wherein the $S_{factor}$ value cmprises the sum of the square of the first acceleration measurements x, the square of the second acceleration measurements y, and the square of the third acceleration measurements z.

16. A method for determining if a body is falling as claimed in claim 15 further comprising determining if a detected fall was accompanied by external force by determining if a combination of the acceleration measurements exceeded a threshold value in a time period prior to the detected fall.

* * * * *